United States Patent [19]

Davis et al.

[11] Patent Number: 5,260,483
[45] Date of Patent: Nov. 9, 1993

[54] PREPARATION OF N-ARYL AMIDES FROM ISOCYANATES

[75] Inventors: Franklin A. Davis, Wynnewood; William E. Starner, Nesquehoning, both of Pa.

[73] Assignee: Drexel University, Philadelphia, Pa.

[21] Appl. No.: 756,420

[22] Filed: Sep. 9, 1991

Related U.S. Application Data

[63] Continuation-in-part of Ser. No. 174,662, Mar. 29, 1988, abandoned.

[51] Int. Cl.$^5$ .................................................. C07C 233/05
[52] U.S. Cl. .................................... 564/218; 564/153; 564/155; 564/183; 564/184; 564/214
[58] Field of Search ............... 564/153, 155, 183, 184, 564/214, 218; 528/48, 49, 55, 56, 58

[56] References Cited

U.S. PATENT DOCUMENTS

| | | | |
|---|---|---|---|
| 2,459,439 | 1/1949 | Lichty et al. | 528/49 |
| 3,350,438 | 10/1967 | Hennig | 560/335 |
| 3,660,326 | 5/1972 | Mallakar | 528/49 X |
| 3,759,873 | 9/1973 | Hadak | 528/58 X |
| 3,799,963 | 3/1974 | Adams | 560/352 |
| 3,896,089 | 7/1975 | Noda et al. | 528/55 |
| 3,984,380 | 10/1976 | Allard | 528/49 |
| 4,061,622 | 12/1977 | Onder | 260/78 R |
| 4,094,866 | 6/1978 | Onder | 260/78 R |
| 4,105,686 | 8/1978 | Raes | 560/351 |
| 4,156,065 | 5/1979 | Onder | 528/51 |
| 4,269,750 | 5/1981 | Lewalter et al. | 528/49 |
| 4,281,095 | 7/1981 | Dunwald et al. | 528/49 |
| 4,395,531 | 7/1983 | Toyoda et al. | 528/57 |
| 4,417,002 | 11/1983 | Liessem | 521/129 |
| 4,467,083 | 8/1984 | Grossman et al. | 528/49 |
| 4,548,970 | 10/1985 | Zecher et al. | 524/99 |
| 4,549,006 | 10/1985 | Zecher et al. | 528/73 |

FOREIGN PATENT DOCUMENTS 46-14674  4/1971  Japan ................................. 528/49

OTHER PUBLICATIONS

Ozaki and Shimada, Nihon Kagaku Zasshi, vol. 80, (1959), pp. 434 and 435; and translation of the complete article.
Nikonova, Vapenen Plact. Massy, 115-122 (1976).
Diechmann, Ber. Dtsch Chem Gas, 309:3052 (1906).
Fry, JACS, vol. 75, pp. 2686-2688 (1975).
Blagbrough et al, Tetrahedron Letters, vol. 27, 11, 1251-4 (1986).
Haller, GR Acad. Sci, vol. 121, 4, pp. 189-193 (1895).
Haller, Comptes Rendus, vol. 120, 1326-9 (1895).
Haller, CR Acad Sci Paris, vol. 64, 23, 1326-9 (1892).
Ozaki et al, Kogyo Kagahu Zasshi, No. 5, vol. 80, 506-9 (1959).
Troparevsky et al, Anales Soc. Quim. Argentina, vol. 61, pp. 227-231 (1973).
Naegeli, Helv. Chim. Acta, vol. 18, 142-160 (1935).
Naegeli, Helv. Chim. Acta, vol. 17, 931-957 (1934).
Sorobin et al, Tv. Mosl. Khim. Technol. Inst., vol. 86, pp. 25-26 (1975).

Primary Examiner—Glennon H. Hollrah
Assistant Examiner—Shailendra Kumar
Attorney, Agent, or Firm—Panitch Schwarze Jacobs & Nadel

[57] ABSTRACT

Methods of producing N-aryl amides comprise reacting an aromatic isocyanate compound with substantially anhydrous carboxylic acid and recovering the resulting N-aryl amide. Additionally, or alternatively, methods of forming N-aryl amides comprise reacting an aromatic isocyanate compound with substantially anhydrous carboxylic acid in the presence of an anhydrous hydrogen halide or hydrolytically unstable halide compound and recovering the resulting N-aryl amide. These reactions may occur in the presence of an aprotic solvent.

17 Claims, No Drawings

PREPARATION OF N-ARYL AMIDES FROM ISOCYANATES

RELATED APPLICATIONS

This is a continuation-in-part (CIP) application of copending U.S. patent application Ser. No. 174,662, filed Mar. 29, 1988, now abandoned, and is related to our copending U.S. patent application "Preparation of N-Aryl Amines From Isocyanates," Ser. No. 174,663, filed Mar. 29, 1988, issued Aug. 20, 1991 as U.S. Pat. No. 5,041,670.

FIELD OF THE INVENTION

The present invention relates to methods of producing N-aryl amides from aromatic isocyanate compounds.

BACKGROUND OF THE INVENTION

The preparation of amides has conventionally consisted of reacting an amine with a carboxylic acid, anhydride or acid chloride. Many methods have been described for such amide production. See, e.g., March, *Advanced Organic Chemistry*, (3d ed., John Wiley and Sons, Inc., 1985) at 1152; Beckwith, *The Chemistry of Formamides*, (Zabicky, ed., London Interscience Publishers, 1970) at 73; and Sandler & Karo, *Organic Functional Group Preparations*, (Academic Press, 1968) at 269. Such methods, however, are generally conducted under extreme heat conditions requiring high energy consumption and producing unsuitable by-product formation. Isolation of the desired amide using these methods is, therefore, difficult. The amide yield in the prior art methods is, in many cases, poor and waste disposal of the by-products is costly and ecologically threatening.

Preparations of an amide by reacting a carboxylic acid with an aryl isocyanate date back to the turn of the century. Such preparations, however, have proven essentially ineffective because of the amide/urea product mixtures thereby obtained. Moreover, an isocyanate reacts generally with a carboxylic acid yielding a mixed carbamic carboxylic anhydride. These anhydrides are relatively unstable and decompose. The resulting mixture is a combination of amide, sym-substituted urea and carboxylic anhydride with an evolution of carbon dioxide. Such unstable mixtures may further dissociate into the starting reagents: isocyanate and carboxylic acid. See Mann and Bruist, *Ber. Dtsch. Chem. Ges.*, 309:3052 (1906).

In Haller, *Complies Rendus*, 121:189 (1895), id. 120:1326 (1895), and id. 64:1326 (1892) it was found that in the reaction of phenyl isocyanate with various carboxylic acids, a mixture of acid anhydride, sym-urea and acid amide were formed. Heating the acid anhydride and the sym-urea to 150° C. or above, generated the acid amide. Vaegeli and Tyabji, *Helv. Chim Acta.*, 18:142 (1935), id. 17:931 (1934), and id. 16:349 (1933) studied the reaction of substituted aromatic isocyanates with carboxylic acids and successfully isolated the mixed anhydride intermediate. They determined that the criteria for mixed anhydride stability was electron withdrawing substitution on the aryl isocyanate. They proposed that decomposition to urea/anhydride occurred through bimolecular disproportion of the mixed anhydride to carbamic anhydride and carboxylic anhydride followed by carbamic anhydride intramolecular rearrangement and $CO_2$ elimination. Amide formation was suggested to occur through an intramolecular rearrangement of the mixed anhydride with $CO_2$ elimination.

Fry, *J. Am. Chem. Soc.*, 75:2686 (1952), Troparevski, et al., *Aneles Asoc. Quim. Argentina*, 61:227 (1973) and Osaki and Shimada, *Kogyo Koga Ku Zasshi*, 80:506 (1959), confirmed that the aromatic isocyanae was the source of the carbon dioxide when forming either amide or urea and anhydride. They determined that the mixed anhydride would decompose to a urea/anhydride formation through bimolecular disproportion to carbamic anhydride and carboxylic anhydride followed by carbamic anhydride intramolecular rearrangement and carbon dioxide elimination. Further, Osaki and Shimada found that the yield of urea/anhydride was increased with increasing electron withdrawing substitution, increasing temperature, introducing ortho substitution, adding a catalyst, and lower carboxylic acid activity. It was further suggested that pure amide would only be formed at temperatures below $-70°$ C.

An isocyanate/carboxylic acid reaction is typified by U.S. Pat. No. 4,417,002, issued to Liessem. Liessem describes forming a foam material in the presence of a blowing agent where formic acid or its salt is reacted with an isocyanate to liberate gas. Liessem disclosed no product distribution or product structure. In addition, U.S. Pat. No. 4,105,686, issued to Raes, describes the use of a carboxylic acid to deactivate a toluene diisocyanate distillation residue to an inert granular solid. Raes did not discuss product distribution or structure. Moreover, reaction temperatures were on the order of 120° C. to 200° C.

The effect of catalysis has been studied in relation to reactions of aromatic isocyanates with carboxylic acids. For example, S. Ozaki et al., *Kogyo Koga Ku Zasshi*, at 80:434 (1959), described the catalytic effect of several compounds, including boron trifluoride etherate, on the reaction of phenyl isocyanate with various carboxylic acids. Several different catalysts, including boron trifluoride etherate, increased the reaction rate, but the product distribution remained the same as without any catalyst. Boron trifluoride showed little catalytic effect.

Sarokin, et al., *Ko. TR. Mosk. Khim. Technol. Inst.* 86:25 (1975) found that catalytic activity in tertiary amine catalysis increased with increasing basicity. Tributylamine and triethylene diamine were noted as exceptions. The same authors presented a paper at the Eleventh Scientific-Technical Conference of Young Scientist and demonstrated that metal catalysts were faster than tertiary amines with a slight preference toward amide formation.

Other conventional methods of reacting aryl isocyanates and carboxylic acids under catalysis include Nikonova and Shoshtaiva, *Vspenen Plast. Massy*, at 115 (1976), where the reaction of phenyl isocyanate with dicarboxylic acids with and without catalysts was investigated. A mixture of urea and amide resulted, dependent on catalyst use. In addition, U.S. Pat. Nos. 4,061,622; 4,094,866; and 4,156,065, issued to Onder, disclose preparing polyamides from aryl diisocyanates and carboxylic acids, using alkoxy metal salts, alkali metal lactamates and hydrocarbylimino derivatives of phosphorous compounds as catalysts.

Further, U.S. Pat. No. 4,395,531, issued to Toyoda et al., describes the preparation of polyamides from aryl diisocyanates and polycarboxylic acids using at least one mono-alkali metal salt of dicarboxylic acid. U.S Pat.

Nos. 4,548,970 and 4,549,006, issued to Zechner et al., describe the preparation of polyamide imides from lactams or polyamides and polyisocyanates and anhydrides using a lactam as an additive.

The prior art methods, however, typically require reaction temperatures in excess of 100° C. to convert urea by-products and the anhydride intermediate to the amide. The catalysts of the prior art are generally ineffective below 100° C. In addition, the prior art methods generally require a two-step procedure: formation of the anhydride and urea, followed by the dehydration reaction of these two intermediates. Low yields and complex product mixtures usually result. Moreover, the catalysts of the prior art are difficult to handle, expensive and poorly efficient in leading to a pure amide product.

In view of the serious deficiencies and inefficiencies of the prior art, it would be desirable to have a method to produce N-aryl amides efficiently, cheaply, easily and with little or no by-product formation.

BRIEF SUMMARY OF THE INVENTION

According to the present invention, methods of producing N-aryl amides comprise reacting an aromatic isocyanate compound with a substantially anhydrous carboxylic acid of the formula: R—COOH, wherein R is a group having at least one carbon atom, the carboxylic acid being present in a molar excess relative to the aromatic isocyanate compound. Additionally, N-aryl amides are produced by reacting an aromatic isocyanate compound with a substantially anhydrous carboxylic acid of the formula: R—COOH, as defined above, in the presence of an anhydrous hydrogen halide or hydrolytically unstable halide compound.

DETAILED DESCRIPTION OF PREFERRED EMBODIMENTS

In accordance with one embodiment of the present invention, an aromatic isocyanate compound is reacted with an about molar excess of substantially anhydrous carboxylic acid of the formula: R—COOH, wherein R is alkyl, substituted alkyl, cycloalkyl, alkylaryl, aryl or arylalkyl (aralkyl). The methods of the present invention require only one step using easy to handle reagents and, where preferred, solvents.

The carboxylic acid is substantially anhydrous in accordance with the present invention. As used herein, the term "substantially anhydrous" will be understood to mean that the carboxylic acid contains less than about 12% by weight water. Commercially available substantially anhydrous carboxylic acid or carboxylic acid dried with, for example, $B_2O_3$ may be used in accordance with the present invention. Preferably, the carboxylic acid contains about 2% or less by weight water (carboxylic acid having an about 2% water content is commonly called 98% carboxylic acid; less than 2% is commonly called anhydrous carboxylic acid). Generally, carboxylic acid having water in amounts greater than those preferred in the present invention causes the formation of large amounts of urea, an undesirable by-product.

Examples of suitable carboxylic acids to produce N-aryl amides include acetic acid, propionic acid, isobutyric acid, trimethylacetic acid, chloroacetic acid, phenylacetic acid, sebacic acid, adipic acid, maleic acid, benzoic acid, nitro benzoic acid, anisic acid, phthalic acid, isophthalic acid and terephthalic acid. It will be appreciated by one skilled in the art, however, that other carboxylic acids having the formula indicated above may be used as the carboxylic acid reagent in accordance with the present invention.

Preferably, the aromatic isocyanate compound is of the formula:

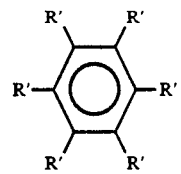

wherein at least one R' group is NCO and the remaining R' groups are selected from the group consisting of hydrogen, alkyl, aryl, cycloalkyl, alkylaryl, arylalkyl, halogen, carboxylic acid, ester, amide and nitrile.

Examples of suitable aromatic isocyanates to produce N-aryl amides include phenyl isocyanate, itolyl isocyanate, chlorophenyl isocyanate, phenylene diisocyanate, 2,4-toluene diisocyanate, 2,6-toluene diisocyanate, methylene bis(phenyl isocyanate) (also called MDI or methylene di-para-phenylene isocyanate) and chloro-m-toluene diisocyanate. One skilled in the art will appreciate, however, that other, similar aromatic isocyanates may be used as the aromatic isocyanate compound reagent in accordance with the present invention.

In one embodiment of the present invention, the reaction of the aromatic isocyanate compound with carboxylic acid occurs in the presence of an aprotic solvent. It is preferred that an aprotic solvent be used in amounts sufficient to permit mobility and/or solubility of the reactants. Accordingly, an aprotic solvent should be used where the mobility and/or solubility of the reagents is restricted. One skilled in the art may readily determine the quantity of aprotic solvent to be used in accordance with the present invention. Examples of suitable aprotic solvents include methylene chloride, chloroform, benzene, toluene, xylene, ethyl ether, methyl ether, tetrahydrofuran, dioxane and acetonitrile. It will be recognized by one skilled in the art, however, that other aprotic solvents may be used in accordance with the present invention.

Where the reaction occurs in the presence of an aprotic solvent, the reaction may occur with heating up to about the boiling point of the carboxylic acid or of the solvent if the boiling point of the solvent is lower than the boiling point of the carboxylic acid. For example, where acetic acid is used in the presence of the aprotic solvent, benzene, heating may occur up to about 80° C. because the boiling point of benzene (80° C.) is lower than the boiling point of acetic acid.

Where an aprotic solvent is not employed in the reaction of the present invention, the reaction may occur with heating up to about the boiling point of the carboxylic acid. It has been found that heating the reaction mixture of the present invention decreases the reaction time necessary to synthesize the desired product and heating the reaction mixture to about 35° C. is presently preferred. Generally, reaction temperatures below about 0° C. and above 100° C. are undesirable. One skilled in the art will appreciate that in this preferred range of reaction temperatures, energy input, in the form of heat, is reduced or eliminated relative to the prior art. In addition, heat sensitive materials, reagents and products may be used or obtained using the methods of the claimed invention.

The reagents are preferably added so that there is an about molar excess of carboxylic acid relative to the isocyanate moieties or functions of the aromatic isocyanate compound. More preferably, the molar ratio of aromatic isocyanate compound to carboxylic acid is about 1:5 to about 1:100. In one preferred embodiment, the molar ratio of aromatic isocyanate compound to carboxylic acid is about 1:10. It will be appreciated by one skilled in the art that as the number of isocyanate moieties of the aromatic isocyanate reagent increases, the quantity of carboxylic acid will generally increase.

It may be desired to conduct the reactions according to the present invention in a vessel under reflux to recover volatilized reactants and solvents during the reaction. One skilled in the art may determine the techniques and apparatus conventionally employed for reflux reactions. Preferably, the reaction mixture is continuously agitated with a magnetic stirrer or other agitation means known in the art. In addition, because carbon dioxide gas is evolved during the reactions of the present invention, it may be desirable to equip the reaction vessel with a vent tube or inert gas purge, such as a nitrogen purge, to rid or collect the evolved gas. One skilled in the art may determine the techniques and equipment desirable for this purpose in accordance with the claimed methods o this invention.

In another embodiment of the present invention, the aromatic isocyanate compound and carboxylic acid are reacted in the presence of a catalyst. When a catalyst is present in the reaction, it is preferred that the molar ratio of isocyanate moieties of the aromatic isocyanate compound to carboxylic acid is about 1:1. The catalyst is added so that there is at least a molar equivalent of the aromatic isocyanate compound and preferably in excess relative to the catalyst. Preferably, the molar ratio of catalyst to aromatic isocyanate compound is about 1:1 to about 1:1000. In one preferred embodiment, for example, the molar ratio of catalyst to aromatic isocyanate compound is about 1:100.

The catalyst is preferably an anhydrous hydrogen halide or hydrolytically unstable halide compound. As used herein, the term "anhydrous" will be understood to mean that the hydrogen halide or hydrolytically unstable compound contains less than about 2% and typically less than about 0.5% by weight of water. The term "hydrolytically unstable halide compound" as used herein, will be understood to mean any halide compound which would generate hydrogen halide under anhydrous conditions. Protic acids in gaseous form, such as gaseous HF or HCl are suitable for the present invention. Anhydrous mineral acids and organometallics may also be used in accordance with the present invention. Examples of such a catalyst include aluminum chloride, ferric chloride, stannous chloride, boron trichloride, boron trifluoride, antimony pentachloride, hydrogen chloride, hydrogen bromide, hydrogen iodide, hydrogen fluoride and dibutyltin dichloride. It will be appreciated by one skilled in the art, however, that other hydrogen halides or hydrolytically unstable halide compound catalysts may be used in accordance with the methods of the present invention.

The course of reaction may be followed by infrared spectroscopy or by the volume of carbon dioxide gas evolved. Preferably, the reaction is allowed to proceed until the evolution of carbon dioxide gas substantially ceases. Analysis of the resulting product may be conducted using conventional techniques, such as gas-liquid chromatography, high-performance liquid chromatography and combustion elemental analysis. One skilled in the art will recognize that other analytical methods may be used to quantify and qualify the resulting product.

In accordance with the methods of the present invention, the N-aryl amide, such as N-phenylacetamide, also called acetanilide, produced generally precipitates out of the reaction mixture. Where a molar excess of carboxylic acid is used as the reagent, there is generally carboxylic acid present after the isocyanate moieties have reacted. Filtering and distillation techniques known in the art, such as vacuum drying and rotary evaporation, may be used to recover the desired N-aryl amide and remove any remaining reactants and solvents. It will be apparent to one skilled in the art that other extraction, distillation, crystallization and filtration techniques may be used to isolate and recover the desired amide.

Product purity in excess of about 98% is obtained using the methods of the present invention. One skilled in the art will recognize the distinction between "purity" and "percent yield" as being the quality of the product for the former term and actual recovery compared to the theoretical yield for the latter term. Generally, the purity of the desired isolated product may be determined by its melting point, as compared with melting point values known in the art. Other qualitative techniques will be apparent to one skilled in the art. Preferably, yields in excess of about 80% are obtained using the methods of the present invention.

The surprisingly high yield and high purity indicate a lack of side reactions and by-products, often present in the prior art. In addition, the high yield and purity of the products formed using the claimed methods herein help to reduce the quantity and cost of raw materials used to produce the desired N-aryl amides.

Isocyanates are known to react with carboxylic acids to form a mixed carbamic carboxylic anhydride. This is illustrated by the following formula:

(I)

While the inventors do not wish to be limited by any particular theory, it is believed that the reaction of the present invention proceeds based on the contrasting rates of the reactions in which the anhydride intermediate may engage. The mixed anhydride intermediate shown in Equation I may undergo intramolecular rearrangement and elimination as illustrated in Equation II:

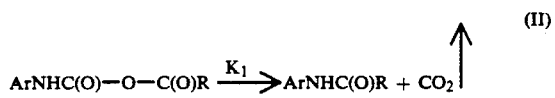

(II)

The anhydride of Equation I may also undergo disproportionation and rearrangement and elimination, which results in urea/carboxylic anhydride formation. This is illustrated by Equation III:

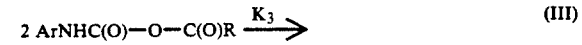

(III)

-continued
$$ArNHC(O)-O-C(O)NHAr + [RC(O)]_2$$
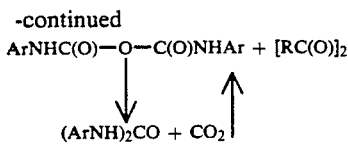
$$(ArNH)_2CO + CO_2\uparrow$$

The rate of intramolecular rearrangement and elimination (shown in Equation II) versus disproportionation and elimination (shown in Equation III) determines the product distribution. Where the aromatic isocyanate and carboxylic acid are present in a substantially equivalent molar ratio in the absence of a catalyst, $K_2$ is substantially similar to $K_3$. Where there is a molar excess of carboxylic acid or where a catalyst is present, the mixed anhydride of Equation I is protonated, diminishing $K_3$ to such an extent that the amide in Equation II is completely formed, (i.e., $K_2 >>> K_3$). $K_2$ may, however, be attenuated when there is a relatively high degree of steric hinderance, reducing the yield of the desired N-aryl amide.

The invention will now be illustrated in further detail by reference to the following specific, non-limiting examples. All parts are parts by weight unless otherwise indicated.

EXAMPLE 1

Phenyl isocyanate (PhNCO) was reacted with each of the following carboxylic acids in a isocyanate:carboxylic acid molar ratio of about 1:10—acetic acid, proprionic acid, isobutyric and pivalic acid. The carboxylic acid was placed in methylene chloride in a vessel equipped with a dropping funnel, a magnetic stirrer, a vent tube and a thermometer. The phenyl isocyanate was added drop-wise to tee solution and stirred for 24 hours at ambient temperature. The volatiles were removed by distillation and the residue was analyzed by gas chromatography to determine product distribution. Table I indicates the resulting products for each carboxylic acid (acetanilide, proprionanilide, isobutyranilide and pivalanilide, respectively).

TABLE I

| PhNCO + Carboxylic Acid | Urea (%) | Amide (%) |
|---|---|---|
| Acetic | 3.0 | 97.0 |
| Proprionic | 12.0 | 88.0 |
| Isobutyric | 48.0 | 52.0 |
| Pivalic | 88.0 | 12.0 |

EXAMPLE 2 (COMPARATIVE)

Phenyl isocyanate and the carboxylic acids identified in Example 1 were reacted in a 1:1 molar ratio following the same procedures and the products were isolated as described in Example 1. Table II shows the respective reactants and products (acetanilide, proprionanilide, isobutyranilide and pivalanilide, respectively) after analysis as in Example 1.

TABLE II

| PhNCO + Carboxylic Acid | Urea (%) | Amide (%) |
|---|---|---|
| Acetic | 40.0 | 60.0 |
| Proprionic | 58.0 | 42.0 |
| Isobutyric | 94.0 | 7.0 |
| Pivalic | 99.0 | 1.0 |

EXAMPLE 3

Phenyl isocyanate was reacted with each of the following carboxylic acids in an isocyanate: carboxylic acid molar ratio of about 1:1 in the presence of anhydrous HCl—acetic acid, proprionic acid and benzoic acid. The reaction and isolation proceeded as in Example 1. Table III shows the reactants and their respective products (acetanilide, proprionanilide and benzoanilide, respectively).

TABLE III

| PhNCO + Carboxylic Acid | HCl:PhNCO (moles) | Urea (%) | Amide (%) |
|---|---|---|---|
| Acetic Acid | 3:100 | * | 100.0 |
| Proprionic Acid | 1:100 | * | 100.0 |
| Benzoic Acid | 1:100 | 26.0 | 74.0 |

*None Detected.

EXAMPLE 4

1.19 g phenyl isocyanate was reacted with 0.6 g acetic acid in a 1:1 molar ratio in the presence of dibutyltin dichloride in methylene chloride (20 parts). The molar ratio of dibutyltin dichloride to phenyl isocyanate was 1:100. The reaction, product isolation and analysis were conducted as in Example 1. A 97.0% yield of acetanilide was obtained (1.20 g).

EXAMPLE 5 (COMPARATIVE)

1.19 g phenyl isocyanate and 0.6 g acetic acid were reacted in a 1:1 isocyanate:acetic acid molar ratio. The reaction, product isolation and analysis were conducted as in Example 1. 0.45 g diphenyl urea and 0.9 g acetanilide were obtained.

EXAMPLE 6

Phenyl isocyanate (2.38 parts) and adipic acid (1.46 parts) in a 2:1 molar ratio were reacted in the presence of HCl using the same procedures as in Example 1. The molar ratio of HCl:phenyl isocyanate was 1:2000. The melting point of the product obtained was 239° C. to 241° C. Table IV indicates the elemental analysis of the product (hexanedianilide).

TABLE IV

| Element | Actual % | Calculated % |
|---|---|---|
| Carbon | 71.44 | 72.95 |
| Hydrogen | 6.73 | 6.80 |
| Nitrogen | 9.47 | 9.45 |

EXAMPLE 7

1.74 g 2,4-toluenediisocyanate and 1.2 g acetic acid were reacted in 1:2 molar ratio in the presence of HCl. The molar ratio of HCl to the diisocyanate was 1:100. The reaction and product isolation were conducted as in Example 1. 1.95 g (96% yield) of the product were recovered. The melting point of the product was 220° C. to 221° C.

The present invention may be embodied in other specific forms without departing from the spirit or essential attributes thereof and, accordingly, reference should be made to the appended claims, rather than the specification, as indicating the scope of the invention.

We claim:

1. A method of producing N-aryl amide, which comprises reacting an aromatic isocyanate compound with a substantially anhydrous carboxylic acid of the formula:-R—COOH, wherein R is alkyl, substituted alkyl, cycloalkyl or aryl, in the presence of an anhydrous hydrogen halide catalyst and recovering the resulting N-arly amide.

2. The method according to claim 1, wherein the catalyst is selected from the group consisting of hydrogen chloride, hydrogen bromide, hydrogen iodide, and hydrogen fluoride.

3. The method according to claim 1, wherein the molar ratio of isocyanate moieties of the aromatic isocyanate compound to carboxylic acid is about 1:1.

4. The method according to claim 1, wherein the molar ratio of catalyst to aromatic isocyanate compound is about 1:1 to about 1:1000.

5. The method according to claim 1, wherein the molar ratio of catalyst to aromatic isocyanate compound is about 1:100.

6. The method according to claim 1, wherein the aromatic isocyanate compound is of the formula:

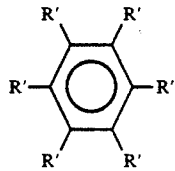

wherein at least one R' group is NCO and the remaining R' groups are selected from the group consisting of hydrogen, alkyl, aryl, halogen, carboxylic acid, ester, amide and nitrile.

7. The method according to claim 6, wherein the aromatic isocyanate compound is selected from the group consisting of phenyl isocyanate, tolyl isocyanate, chlorophenyl isocyanate, phenylene diisocyanate, 2,4-toluene diisocyanate, 2,6-toluene diisocyanate, methylene bis(phenyl isocyanate) and chloro-m-toluene diisocyanate.

8. The method according to claim 1, wherein the carboxylic acid is selected from the group consisting of acetic acid, propionic acid, isobutyric acid, trimethylacetic acid, chloroacetic acid, phenylacetic acid, sebacic acid, adipic acid, maleic acid, benzoic acid, nitro benzoic acid, anisic acid, phthalic acid, isophthalic acid and terephthalic acid.

9. The method according to claim 1, wherein the reaction occurs in the presence of an aprotic solvent.

10. The method according to claim 9, wherein the aprotic solvent is selected from the group consisting of methylene chloride, chloroform, benzene, toluene, xylene, ethyl ether, methyl ether, tetrahydrofuran, dioxane and acetonitrile.

11. The method according to claim 9, wherein the reaction occurs with heating up to about the boiling point of the carboxylic acid or of the solvent if the boiling point of the solvent is lower than the boiling point of the carboxylic acid.

12. The method according to claim 1, wherein the reaction occurs with heating up to about the boiling point of the carboxylic acid.

13. The method according to claim 1, wherein the reaction occurs with heating to a temperature of about 20° C. to about 100° C.

14. The method according to claim 1, wherein the reaction proceeds until $CO_2$ evolution substantially ceases.

15. The method according to claim 2, wherein phenyl isocyanate is reacted with acetic acid in the presence of dibutyltin dichloride, the molar ratio of phenyl isocyanate to dibutyltin dichloride being about 100:1, in methylene chloride at atmospheric pressure with heating to a temperature of about 35° C. until $CO_2$ evolution substantially ceases.

16. The method according to claim 1, wherein phenyl isocyanate is reacted with acetic acid in the presence of hydrogen chloride, the molar ratio of phenyl isocyanate to hydrogen chloride being about 100:1, in methylene chloride at atmospheric pressure until $CO_2$ evolution substantially ceases.

17. A method of producing N-aryl amide, which comprises reacting an aromatic isocyanate compound with a substantially anhdrous carboxylic acid of the formula:R—COOH, wherein R is alkyl, substituted alkyl, cycloalkyl or aryl, in the presence of an anhydrous hydrolytically unstable halide catalyst selected from the group consisting of aluminum chloride, ferric chloride, stannous chloride, antimony pentachloride, and dibutyltin dichloride, and recovering the resulting N-aryl amide.

* * * * *